US00PP32765P2

(12) United States Plant Patent
Olesen

(10) Patent No.: US PP32,765 P2
(45) Date of Patent: Jan. 26, 2021

(54) CLIMBING ROSE PLANT NAMED 'POULCY038'

(50) Latin Name: ***Rosa* hybrid**
Varietal Denomination: Poulcy038

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/602,248

(22) Filed: Sep. 4, 2019

(51) Int. Cl.
*A01H 5/02* (2018.01)
*A01H 6/74* (2018.01)

(52) U.S. Cl.
USPC ..... Plt./111
CPC ..... *A01H 6/749* (2018.05)

(58) Field of Classification Search
USPC ..... Plt./111
CPC ..... A01H 6/749
See application file for complete search history.

(56) References Cited

PUBLICATIONS

'Mapale TM' Rose, HelpMeFind at https://www.helpmefind.com/rose/l.php?l=2.81677.0, downloaded on May 29, 2020.*
UPOV hit on QZ PBR 20182410, filed Sep. 24, 2018.*

* cited by examiner

*Primary Examiner* — Anne Marie Grunberg

(57) ABSTRACT

A new garden rose plant of the Climbing class which has abundant, yellow flowers and attractive foliage. This new and distinct variety has shown to be uniform and stable in the resulting generations from asexual propagation.

2 Drawing Sheets

Botanical designation: *Rosa* hybrid.
Variety denomination: 'Poulcy038'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2006 and the resulting seeds were planted in a controlled environment in Fredensborg, Denmark. The new variety, named 'Poulcy038', originated as a single seedling from the stated cross.

The new variety may be distinguished from its male pollen parent and female seed parent primarily by the following characteristics. The male pollen parent plant has the growth habit of a floribunda rose plant, while the new variety has the growth habit of a climbing rose plant. The female seed parent plant has near white flowers while the new variety has yellow flowers.

The objective of the hybridization of this rose variety was to create a new and distinct variety with unique qualities, such as:

1. Uniform and abundant yellow flowers;
2. Vigorous, but compact growth when propagated on its own roots;
3. Exceptional disease resistance.
4. Reduced apical dominance in flowering habit. The new variety consistently produces flowers evenly from the lower branches to the top of the plant.

This combination of qualities is not present in previously available commercial cultivars of this type, known to the inventor, and distinguish 'Poulcy038' from all other varieties of which we are aware.

As part of the rose development program, Mogens N. Olesen germinated the seeds from the aforementioned hybridization during winter of 2006 and conducted evaluations on the resulting seedlings in a controlled environment in Fredensborg, Denmark. 'Poulcy038' was selected in the spring of 2007 by the inventor as a single plant from the progeny of the aforementioned hybridization.

Asexual reproduction of 'Poulcy038' by rooted cuttings was first done by Mogens N. Olesen in the nursery in Fredensborg, Denmark in July, 2007. This initial and other subsequent asexual propagations conducted in controlled environments have demonstrated that the characteristics of 'Poulcy038' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcy038'.

Specifically illustrated in FIG. 1 of the drawings are open flowers viewed from above and from the side, a flower bud upon opening, flower petals detached, and sepals detached showing reproductive flower parts.

Figure 1:
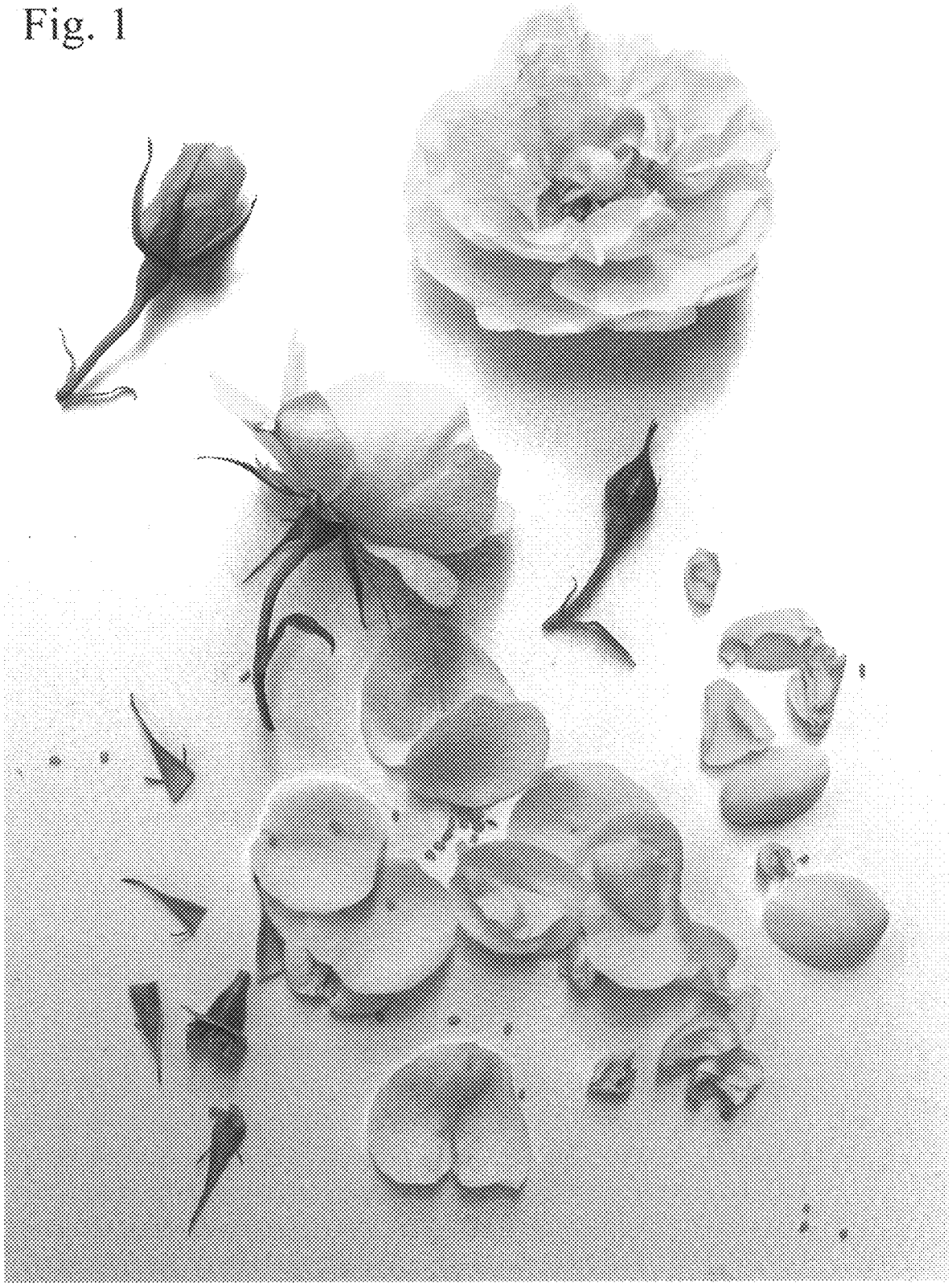
Figure 2:
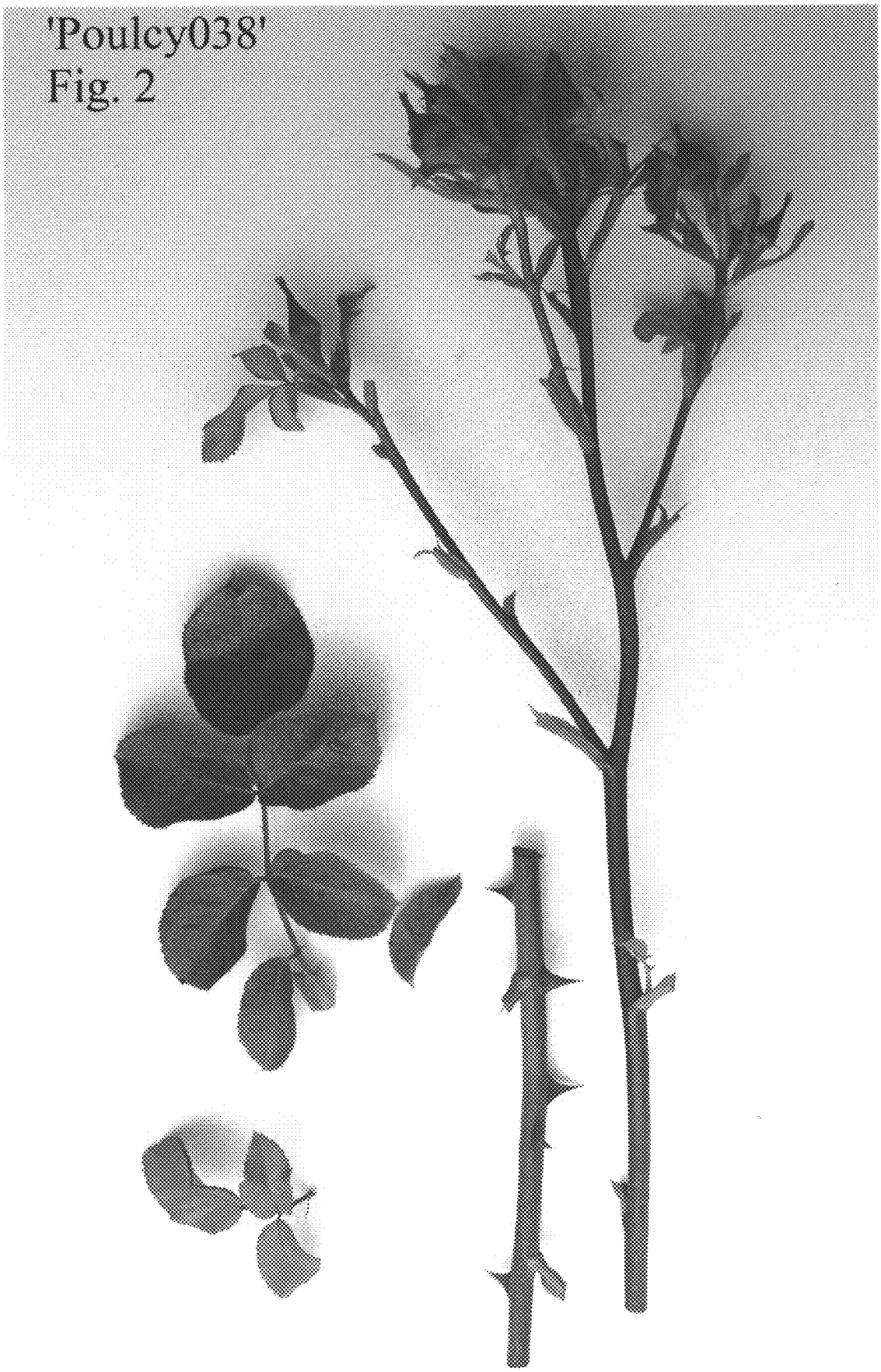

Specifically illustrated in FIG. 2 of the drawings are juvenile and mature leaves, bare stems exhibiting thorns, and clusters of flower buds on a branch. Plants shown are 2 years of age.

DETAILED DESCRIPTION OF THE VARIETY

The following is a description of 'Poulcy038', as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulcy017', U.S. Plant Pat. No. 26,601 are compared to 'Poulcy038' in Chart 1.

CHART 1

| | 'Poulcy038' | 'Poulcy017' |
|---|---|---|
| Petal Count | 40 petals | 27 petals |
| Flower Diameter | 75 mm | 40 to 45 mm |
| General Tonality of Flower Color | Yellow Group 10B | Yellow Group 8B |

FLOWER AND FLOWER BUD

Blooming habit: Continuous.

Flower bud:

*Size.*—Upon opening, 25 mm in length from base of receptacle to end of bud. Bud diameter is 11 mm.

*Bud form.*—Ovoid.

*Bud color.*—As sepals divide petals are Yellow-Orange Group 22A.

*Sepal inner surface.*—Color: Yellow-Green Group 146D. Surface: Lightly pubescent.

*Sepal outer surface.*—Color: Yellow-Green Group 144A. Texture: Smooth.

*Sepal shape.*—Apex: Cirrhose. Base: Flat at union with receptacle.

*Sepal margin.*—Margins have moderate foliaceous appendages on three of the five sepals.

*Sepal size.*—27 mm long, 6 mm wide.

*Receptacle.*—Texture: Smooth. Size: 10 mm in height, 7 mm wide. Color: Yellow-Green Group 144A. Shape: Globular.

*Pedicel.*—Surface: Smooth. Length: 23 mm. Diameter: 2.5 mm on average. Color: Yellow-Green Group 144A. Strength: Strong.

*Peduncle.*—Length: 7 to 16 cm. Diameter: About 3.5 mm. Color: Yellow-Green Group 144B with intonations of Greyed-Red Group 180B. Texture: Smooth.

Flower bud development: Flower buds are borne in clusters of about 5 flower buds per stem.

Flower bloom:

*Fragrance.*—Moderate.

*Duration.*—The blooms have a duration on the plant of approximately 10 days. Petals fall cleanly away from plant after flowers have fully matured.

*Size.*—Flower diameter is 75 mm when open. Flower depth is 30 mm.

*Flower shape.*—Open cup, double flower, with petals that curve out from the center.

*Shape of flower, side view.*—The upper portion is a flat convex. The lower portion is flattened and concave.

Petalage: Under normal conditions, flowers have about 40 petals.

General tonality of flower: Open flowers are Yellow Group 10B.

Petal color:

*Upon opening, inner and outer petals.*—Upper surface: Yellow Group 10B. Lower surface: Yellow Group 10C with intonations of Yellow-Orange Group 18A.

*Basal petal spots, upon opening.*—Upper surface: Yellow Group 9A. Lower surface: Yellow Group 9A.

*After opening, outer and inner petals.*—Upper surface: Yellow Group 10B. Lower surface: Yellow Group 10C with intonations of Yellow-Orange Group 18A.

*Basal petal spots, after opening.*—Upper surface: Yellow Group 9A. Lower surface: Yellow Group 9A.

Petals:

*Petal reflex.*—None.

*Margin.*—Entire and uniform. Moderate undulations.

*Shape.*—Broad and elliptic. Apex shape: Rounded. Base shape: Acute.

*Size.*—41 mm (l)×45 mm (w).

*Texture.*—Smooth.

*Thickness.*—Average.

Petaloids:

*Size.*—12 mm (l) by 9 mm (w).

*Quantity.*—

*Shape.*—Elliptical with an acute base and rounded apices.

*Color.*—Upper surface is Yellow Group 10B. Lower petaloid surface is Yellow Group 10C with intonations of Yellow-Orange Group 18A.

Reproductive flower parts:

*Pollen.*—None observed.

*Anthers.*—Size: 3 mm in length. Color: Yellow Orange Group 15D. Quantity: 47 on average.

*Filaments.*—Color: Orange-Red Group 34B. Length: 4 mm.

*Pistils.*—Length: 4 mm. Quantity: 26 on average.

*Stigmas.*—Color: Greyed-Yellow Group 160A.

*Styles.*—Color: Greyed-Yellow Group 160A.

*Location of stigmas.*—Inferior in location relative to the length of the filaments and the height of the anthers.

*Hips.*—None Observed.

PLANT

Plant growth: Climbing. Plants are about 150 cm in height, and 100 cm wide.

Stems:

*Color of juvenile growth.*—Yellow-Green Group 144B.

*Color of mature growth.*—Yellow-Green Group 144A.

*Length.*—Canes are about 40 cm from the base of the plant to the flowering portion.

*Diameter.*—About 9 mm.

*Internodes.*—On mature canes about 70 mm between nodes.

*Surface texture.*—Young wood: Smooth. Older wood: Smooth.

Long prickles:

*Incidence.*—About 8 prickles per 10 cm of stem.

*Size.*—Average length of prickles on mature stems is 10 mm.

*Shape.*—Upper portion is linear. Lower portion is concave.

*Color.*—Juvenile prickles: Greyed-Red Group 180A. Mature prickles: Greyed-Red Group 180A.

Plant foliage:

*Compound leaf.*—110 mm (l)×70 (w).

*Quantity.*—2 leaves per 10 cm of stem on average.

*Leaf bearing angle to the stem.*—45 degrees.

*Color of juvenile foliage.*—Upper side: Yellow-Green Group 144A with intonations of Greyed-Red Group 178B at the margins. Lower side: Yellow-Green Group 144A with intonations of Greyed-Red Group 178B.

*Color of mature foliage.*—Upper side: Yellow-Green Group 144A. Lower side: Yellow-Green Group 146C.

Plant leaves and leaflets:

*Stipules.*—Size: 11 mm long, 3 mm wide. Quantity: 2 per compound leaf. Shape: Linear, slightly broad based with outward extending apices. Margins: Finely serrated. Color: Yellow-Green Group 144A.

*Petiole.*—Length: 15 mm. Diameter: 2 mm. Upper surface color: Yellow-Green Group 144A. Lower surface color: Yellow-Green Group 144A.

*Rachis.*—Length: About 60 mm. Upper surface color: Yellow-Green Group 144A. Lower surface color: Yellow-Green Group 144A.

*Leaflet.*—Quantity: Normally 5 to 7 leaflets. Margins: Serrated. Size: Terminal leaflets are about 42 mm long, 31 mm wide. Shape: Generally elliptical. Base: Rounded. Apex: Mucronate. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

We claim:

1. A new and distinct variety of rose plant of the Climbing rose class named 'Poulcy038', substantially as illustrated and described herein, due to its abundant yellow flowers, disease resistance, and extended period of bloom.

* * * * *

'Poulcy038'

'Poulcy038'